(12) United States Patent
Meier et al.

(10) Patent No.: US 8,550,373 B2
(45) Date of Patent: Oct. 8, 2013

(54) FRAGRANCE RELEASE SYSTEM HAVING AN OPTIMIZED WICK

(75) Inventors: Frank Meier, Düsseldorf (DE); Daniela Poethkow, Krefeld (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 200 days.

(21) Appl. No.: 13/100,677

(22) Filed: May 4, 2011

(65) Prior Publication Data

US 2011/0284654 A1 Nov. 24, 2011

(30) Foreign Application Priority Data

May 7, 2010 (DE) .......................... 10 2010 028 747

(51) Int. Cl.
*A24F 25/00* (2006.01)
(52) U.S. Cl.
USPC .................................. 239/44; 239/43; 239/45
(58) Field of Classification Search
USPC ............... 239/44, 45, 56, 34, 6, 43; 502/401; 604/368
See application file for complete search history.

(56) References Cited

U.S. PATENT DOCUMENTS

| | | | | |
|---|---|---|---|---|
| 2,787,496 | A * | 4/1957 | Skaist | 239/45 |
| 4,915,301 | A * | 4/1990 | Munteanu | 239/45 |
| 5,242,111 | A * | 9/1993 | Nakoneczny et al. | 239/47 |
| 6,446,880 | B1 * | 9/2002 | Schram et al. | 239/45 |
| 6,871,794 | B2 * | 3/2005 | McEwen | 239/44 |
| 2010/0116898 | A1 * | 5/2010 | Litten-Brown et al. | 239/145 |

* cited by examiner

*Primary Examiner* — Davis Hwu
(74) *Attorney, Agent, or Firm* — David K. Benson

(57) ABSTRACT

The apparatus comprises a fragrance release system comprising a wick, at least one diffuser, the surface area of the diffuser in contact with ambient air being larger than the surface area of the wick in contact with ambient air, and a container to hold the wick, a fragrance preparation that is stored in the container, the fragrance preparation being transported through the wick to the diffuser by capillary action against the direction of gravity when the wick is housed in the container, wherein the substantially cylindrical wick is formed from at least two mutually different plant-based fibrous materials, the first material forming a core and the second material surrounding this core, and the difference between the contact angle of the core material and that of the material surrounding the core relative to water being at least 10°, the core material having the small contact angle, preferably between 0° and 90°, relative to water.

20 Claims, No Drawings

FRAGRANCE RELEASE SYSTEM HAVING AN OPTIMIZED WICK

CROSS-REFERENCE TO RELATED APPLICATIONS

This application claims the benefit of application 10 2010 028 747.4 (DE), filed on May 7, 2010, hereby incorporated by reference.

The invention relates to a diffusion-driven fragrance release system having an improved wick. In particular the invention relates to an optimized wick in conjunction with an indicator showing the activation and/or usage of the fragrance release system.

Diffusion-driven fragrance release systems are sufficiently known from the prior art. In particular, systems based on a wick and a container filled with a liquid, fragrance-containing preparation are known in which the wick is introduced into the container and the preparation is transported to the surfaces of the wick against the direction of gravity owing to the capillary forces of the wick, from where the fragrance transported in this way is released to the environment, usually via evaporation.

In addition to having an acceptable fragrance transport rate, the wick must frequently also exhibit an adequate mechanical stability to enable it to be stored in a free-standing manner, for example, in a fragrance-containing container without the wick softening due to the absorption of liquid fragrance preparation and ultimately bending.

OBJECT OF THE INVENTION

The object of the invention is therefore to provide a fragrance release system having an optimized wick which in addition to an acceptable substance transport rate also exhibits an adequate mechanical stability.

This object is achieved by a fragrance release system having the features of claim 1.

The fragrance release system according to the invention comprises a wick and at least one diffuser, the surface area of the diffuser in contact with ambient air being larger than the surface area of the wick in contact with ambient air. The diffuser thus brings about an increase in the size of the surface area via which the fragrance is released to the environment.

The fragrance release system according to the invention also comprises a container to hold the wick and a fragrance preparation that is stored in the container, the fragrance preparation being transported through the wick to the diffuser by capillary action against the direction of gravity when the wick is housed in the container. The diffuser is preferably positioned at the end of the in particular stem-shaped or cylindrical wick facing away from the container.

The fragrance preparation that is stored in the container is transported through the wick to the diffuser by capillary action against the direction of gravity when the wick is housed in the container.

The substantially cylindrical wick contains at least two mutually different plant-based fibrous materials, the first material forming a core and the second material surrounding this core, and the difference between the contact angle of the core material and that of the material surrounding the core relative to water being at least 10°, the core material having the small contact angle, preferably between 0° and 90°, relative to water. Adequate stability and substance transport properties of the wick are achieved in this way.

It is particularly preferable for the difference between the contact angle of the core material and that of the material surrounding the core relative to water to be at least 10°. The contact angle is defined as the angle formed by a drop of liquid—in this case water—on the surface of a solid—in this case the core material or the material surrounding the core—to this surface.

For example, the contact angle of the core material (e.g. a filter paper) to water can be 0°, which corresponds to a complete wetting of the core material with water. The contact angle of the material surrounding the core, made from *Aeschynomene aspera* for example, is 30° to 45°, which corresponds to a partial, drop-like wetting of the surrounding material.

Goniometers are conventionally used to measure contact angle. To this end, a drop of a known liquid—in this case water—is placed on a solid surface to be examined. An optical device is used to locate the angle formed by the edge of the drop with the substrate over the surface of the drop. An exact description of the method for measuring the contact angle can be found by the person skilled in the art in ASTM D 724-94 Standard Test Method for Surface Wettability of Paper (Angle-of-Contact Method).

The substantially cylindrical wick is preferably formed from at least two mutually different plant-based fibrous materials, the first material with a cotton fiber content of more than 20% forming the core of the wick and the second material formed from a cellulose-based material, in particular *Aeschynomene aspera*, surrounding this core. In this way an acceptable substance transport through the core of the wick can be achieved, while the mechanical stability of the wick is obtained by the sheath of cellulose-based material surrounding the core.

It is furthermore preferable for the difference in the capillary rises of the core material and the material surrounding the core to be at least 10 mm.

For example, the capillary rise with water after 120 s is 30 mm for the core material (filter paper). The capillary rise for the material surrounding the core, consisting in particular of *Aeschynomene aspera*, is 0 mm.

The capillary rise can be measured in accordance with DIN 53923 and/or DIN 53924 (measured with water) using strips measuring approx. 10 cm in length and 1 cm in width.

Suitable materials for the core of the wick are for example filter papers MN616 or MN601 from Macherey-Nagel, Düren, Germany.

The core preferably has a diameter of 0.1 to 1 cm, preferably 0.2 to 0.5 cm.

The sheath is preferably cylindrical with an internal and an external diameter. The sheath formed from the second material advantageously lies with its inner side directly against the outer surface of the core. The internal diameter of the sheath is preferably between 0.1 and 1 cm, preferably between 0.2 and 0.5 cm. The external diameter is preferably 0.7 to 1.2 cm, particularly preferably 0.8 to 1 cm. The sheath may be formed from one or more layers of the second material.

The exclusive use of natural materials to form the wick makes it easy to dispose of in an environmentally friendly manner, for example by composting.

In a preferred embodiment of the invention, within a capillary flow path of the fragrance preparation through the wick and/or diffuser at least one reservoir is provided, through which the fragrance preparation can flow and which contains at least one dye that can be dissolved by the fragrance preparation.

Within the meaning of this application reservoir means a defined volume of space within the fragrance release system, within which at least one dye is stored.

The dye contained in the reservoir is dissolved by the fragrance preparation as it flows through the reservoir, due to capillary action in particular, and the fragrance preparation is thus colored along its movement along its further diffusion path through the wick and/or the diffuser by the dye that is transported along with it.

It is further advantageous for the diffuser to have a substantially circular base when viewed from above, such that the distance between the wick, which in particular is connected to the diffuser in the middle of the circular base, and the outer edge of the diffuser is substantially constant. This results in substantially identical diffusion path lengths and times over the base.

In order to bring about a greater release of fragrance, it can be advantageous for the ratio of the surface area of the diffuser in contact with ambient air to the surface area of the wick in contact with ambient air to be between 1000:1 and 1.25:1, preferably between 125:1 and 2.5:1.

The diffuser is preferably formed from a plurality of substantially uniform plates, one end of the plates being fixed in or to the wick. In accordance with a preferred embodiment of the present invention, the diffuser may be formed from at least two groups of mutually different plates.

The number of plates is in particular at least 6, preferably at least 50, particularly preferably at least 100.

In a further particularly advantageous embodiment of the invention the plates each have a surface area, consisting of the top and bottom of a plate, of 0.5 to 100 cm$^2$, preferably 1 to 75 cm$^2$, particularly preferably 2 to 50 cm$^2$.

It is further possible for the plates to be arranged in an alternate (acyclic) or verticillate (cyclic) pattern on the wick axis.

The angle between two adjacent plates is preferably between 3° and 140°, preferably between 4° and 137.5°.

In a further embodiment of the invention the diffuser formed from the plurality of plates can have at least one, preferably two, particularly preferably three planes of symmetry.

The person skilled in the art can use suitable dyes from the prior art for the reservoir.

It is furthermore particularly advantageous that when the reservoir is not yet housed in the container it is positioned in the wick and/or in the diffuser so that it is not visible from outside.

It is also conceivable in principle for dye reservoirs each containing mutually different dyes to be provided in the wick and diffuser.

The dye can be introduced into the wick and/or diffuser by the methods known to the person skilled in the art from the prior art, for example by infusion (injection), such that a reservoir of dye is formed there.

The invention is described in more detail below by reference to an exemplary example.

In a first embodiment example the fragrance release system consists of a container for a fragrance preparation containing perfume oil, a wick, a diffuser arranged on the wick, and a fragrance oil preparation containing perfume oil for use with the fragrance release system.

A glass vessel with an opening approx. 1.5 cm wide was used as the container. In principle, however, porcelain or ceramic vessels are also suitable.

Any preparations which have been developed for the fragrancing of rooms in wick systems can be used as the fragrance preparation containing perfume oil for example from perfume houses such as Bell Flavors and Fragrances, Firmenich, Givaudan, International Fragrance & Flavors, Symrise, or Takasago. In such fragrance preparations, the content of perfume oil in the solvent is conventionally between 2 and 10%.

The conventional dyes used in washing and cleaning agents, for example, may be used as dyes.

A mixture of water and ethanol is suitable as the solvent of the fragrance-containing preparation. However, isopropanol, dipropylene glycol, diethyl phthalate, isopropyl myristate, benzyl benzoate, 2-(2-ethoxy-ethoxy)-1-ethanol, or ethyl citrate can also be used, either alone or as a mixture.

A natural plant material is particularly suitable for use as the wick and/or diffuser material. The plant material used is *Aeschynornene aspera* from the Fabaceae family.

The length of the wick is preferably approx. 8 cm, with a diameter of approx. 1 cm. The diameter of the wick is chosen such that it can readily be introduced into the opening of the container storing the fragrance-containing preparation and that the diffuser projects a few centimeters out of the opening. The container and the wick as well as the diffuser are configured and matched to one another in such a way that the container is stable when the wick and diffuser are inside it. The diameter of the diffuser is approx. 5 cm.

The dyes can be selected for example from the following list, which shows the dyes in the C.I. (Color Index) with their generic names:

Solvent Red 135, Acid red 18, Food red 7, Azo complex, Pigment Red 112, Pigment violet 23, Basic violet, Acid red 52, C.I. Food Yellow 3, Food red 9, Pigment red 112, FD&C yellow 5, Aluminum lake, Pigment yellow 1, Sunset yellow, Acid Yellow 5, Basic Yellow 28, Yellow 97, DC yellow 8, Acid green 25, Green 7, Patent Blue AE E133, Direct blue 86, Acid Blue 182, Acid blue 9, Acid blue 3, Basic blue 3, Acid blue 225, Blue 15:1, Blue 15:3, Acid blue 80, Acid blue 7, Acid blue 9, FD & C blue No. 1, Food Blue 2, VAT Red 1, Acid red 27, Solvent yellow 16, Pigment Yellow 1, Acid Yellow 9, Pigment green 7, Pigment blue 15:1, Pigment blue 15, Acid blue 9, Acid red 52, Basic Violet 10, Basic Violet 10, Basic violet 10, Basic violet 10, Reactive Red 24:1, Acid yellow 232, Acid red 274, Acid brown 413, Acid red 414, Acid red 52, Acid red 18, Food red 7, Acid red 52, Basic violet 10, FD&C No. 40, Food Red 17, Acid red 1, Food red 10, Solvent yellow 179, Disperse yellow 201, Acid yellow 36, Pigment yellow 147, Acid yellow 17, Acid orange 7, Yellow 81, Reactive yellow 161, Food yellow 3, Acid yellow 218, Solvent yellow 174, Acid yellow 3, Reactive yellow 25, Reactive yellow 25, Food yellow 13, Solvent yellow 93, Solvent Orange, Pigment green 7, Solvent Green 3, Solvent Green 7, Pigment green 7, Pigment Green 7, Pigment Green 7, Acid green 25, Food Yellow 4, Acid Yellow 23, Direct blue 86, FD&C Blue No. 1, Solvent blue 35, Acid blue 9, Acid Blue 104, Pigment blue 15:1, Acid blue 182, Solvent Blue 35, Acid blue 182, Acid blue 9, Blue 35, Reactive blue 197, Pigment blue 29, Pigment Blue 15:1, Acid blue 9, Food Blue 2, Acid blue 9.

The dye is added to the inner layers of the wick, for example by impregnating these layers with the dye or by injecting the dye into these layers. The outer layers are preferably not provided with the dye of the inner layers, so that a user does not see the inner layers of the wick containing the dye or cannot come into contact with them when using the wick.

The invention claimed is:

1. A fragrance release system comprising:
   (a) a substantially cylindrical wick having a surface area in contact with ambient air, said wick comprising an inner core comprising a first plant-based fibrous material and an outer sheath comprising a second plant-based fibrous material, said sheath in contact with said core, said first and second plant-based materials being mutually different;

(b) at least one diffuser having a surface area in contact with ambient air and comprising a plurality of substantially uniform plates, each of said plates having an end fixed into or onto said wick, said surface area of said diffuser in contact with ambient air being greater than said surface area of said wick in contact with ambient air;

(c) a container with an opening configured to position said wick partially there through; and (d) a fragrance preparation stored within said container, said preparation being transported through said wick to said diffuser by capillary action against the direction of gravity when said wick is positioned in said container in contact with said preparation; and wherein the contact angle of said first plant-based fibrous material is less than the contact angle of said second plant-based fibrous material, and wherein the difference in said contact angles is at least 10°.

2. The system of claim 1 wherein the contact angle of said first plant-based fibrous material relative to water is between about 0° and 90°.

3. The system of claim 1 wherein said first plant-based fibrous material has a cotton fiber content of more than 20%, and wherein said second plant-based material comprises a cellulose-based material.

4. The system of claim 3 wherein said cellulosic second plant-based fibrous material is obtained from *Aeschynomene aspera*.

5. The system of claim 1, further comprising at least one reservoir containing at least one dye, said reservoir positioned along the capillary flow path of said fragrance preparation either in said container, in said wick, or in said diffuser, such that said fragrance preparation dissolves said dye upon movement of said preparation by capillary action past said reservoir.

6. The system of claim 5 wherein said reservoir is positioned in said wick or in said diffuser such that said dye is not visible from outside said system.

7. The system of claim 1 wherein said diffuser has a substantially circular base when viewed from above.

8. The system of claim 1 wherein the ratio of said surface area of said diffuser in contact with ambient air to said surface area of said wick in contact with ambient air is between about 1000:1 and about 1.25:1.

9. The system of claim 8 wherein said ratio of said surface areas is between about 125:1 and about 2.5:1.

10. The system of claim 1 wherein said diffuser is formed from at least two groups of mutually different plates.

11. The system of claim 1 wherein said plates are at least 6 in number.

12. The system of claim 1 wherein said plates are at least 50 in number.

13. The system of claim 12 wherein said plates are at least 100 in number.

14. The system of claim 1 wherein each plate has a total surface area of from about 0.5 to about 100 $cm^2$.

15. The system of claim 14 wherein each plate has a total surface area of from about 1 to about 75 $cm^2$.

16. The system of claim 15 wherein each plate has a total surface area of from about 2 to about 50 $cm^2$.

17. The system of claim 1 wherein said plates are arranged in an alternate pattern or a verticillate pattern on the wick axis.

18. The system of claim 1 wherein the angle between two adjacent plates is from about 3° to about 140°.

19. The system of claim 1 wherein said diffuser comprised of said plates has from one to three planes of symmetry.

20. The system of claim 6 wherein mutually different dyes are provided in said wick and in said diffuser.

* * * * *